United States Patent
Chheda et al.

(10) Patent No.: US 9,617,200 B2
(45) Date of Patent: Apr. 11, 2017

(54) PROCESS FOR PREPARATION OF TERTIARY ALKYL PRIMARY AMINES

(71) Applicants: Dow Global Technologies LLC, Midland, MI (US); Rohm and Haas Company, Philadelphia, PA (US)

(72) Inventors: Bharati D. Chheda, Houston, TX (US); John G. Pendergast, Jr., Pearland, TX (US); Sivam Rangavajjula, Audubon, PA (US); Daniel M. Trauth, Crystal Lake, IL (US)

(73) Assignees: ROHM AND HAAS COMPANY, Philadelphia, PA (US); DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 14/781,627

(22) PCT Filed: Apr. 2, 2014

(86) PCT No.: PCT/US2014/032672
§ 371 (c)(1),
(2) Date: Oct. 1, 2015

(87) PCT Pub. No.: WO2014/165586
PCT Pub. Date: Oct. 9, 2014

(65) Prior Publication Data
US 2016/0060207 A1 Mar. 3, 2016

Related U.S. Application Data

(60) Provisional application No. 61/807,834, filed on Apr. 3, 2013.

(51) Int. Cl.
C07C 209/00 (2006.01)
C07C 209/62 (2006.01)
C07C 209/44 (2006.01)

(52) U.S. Cl.
CPC .......... *C07C 209/62* (2013.01); *C07C 209/44* (2013.01)

(58) Field of Classification Search
None
See application file for complete search history.

(56) References Cited

U.S. PATENT DOCUMENTS

| | | | | |
|---|---|---|---|---|
| 3,432,552 A | * | 3/1969 | Kiefer | C08K 5/17 525/332.5 |
| 4,732,609 A | * | 3/1988 | Frey | B01J 41/043 204/DIG. 13 |
| 5,527,949 A | * | 6/1996 | Agarwal | C07C 67/22 560/129 |

* cited by examiner

*Primary Examiner* — Patrick Lewis
(74) *Attorney, Agent, or Firm* — Kenneth Crimaldi

(57) ABSTRACT

A method for producing an amine. The first step is contacting a cyanide, an acid, water and a substrate compound capable of generating a carbonium ion by reaction with the acid to generate a first reaction intermediate. The second step is contacting the first reaction intermediate with water to form a second reaction intermediate. The third step is removing cyanide present in the second reaction intermediate to a concentration less than 10 ppm. The fourth step is contacting the second reaction intermediate with an alkali metal hydroxide to form the amine.

7 Claims, No Drawings

PROCESS FOR PREPARATION OF TERTIARY ALKYL PRIMARY AMINES

This invention relates to a method for preparation of tertiary alkyl primary amine compounds with reduced waste costs.

Methods for preparation of tertiary alkyl primary amines are known. For example, U.S. Pat. No. 5,527,949 discloses a method for contacting a nitrile, an acid, water and a compound capable of generating a carbonium ion. However, this method still produces cyanide waste products that require expensive treatment for disposal.

The problem addressed by this invention is to find an improved method for preparation of tertiary alkyl primary amines with reduced cyanide waste.

STATEMENT OF INVENTION

The present invention provides an improved method for producing an amine; said method comprising steps of: (a) contacting hydrogen cyanide or a salt thereof, an acid, water and a substrate compound capable of generating a carbonium ion by reaction with the acid to generate a first reaction intermediate; (b) contacting the first reaction intermediate with water to form a second reaction intermediate; (c) removing cyanide present in the second reaction intermediate to a concentration less than 10 ppm; and (d) contacting the second reaction intermediate with an alkali metal hydroxide to form the amine.

DETAILED DESCRIPTION

Percentages are weight percentages ("wt %") and temperatures are in ° C., unless specified otherwise. An "alkyl" group is a saturated hydrocarbyl group having from one to thirty carbon atoms in a linear, branched or cyclic arrangement, preferably linear or branched. Concentrations expressed in parts per million ("ppm") are calculated on a weight/weight basis.

In a first step of the method of the present invention, a cyanide and a substrate capable of generating a carbonium ion by reaction with a strong acid are heated in the presence of water and a strong acid HA to generate a first reaction intermediate.

Suitable substrate compounds for the method of the present invention are those known as substrates for the Ritter reaction and include, for example, alcohols, alkenes, aldehydes, ketones, ethers, see, generally, L. I. Krimen and D. J. Cota, "The Ritter Reaction", Organic Reactions, Vol. 17, 1969, pp. 213-325. Preferably, the substrate compound is an alcohol (e.g., benzyl alcohol, isopropanol, cyclohexanol, t-butanol, t-amyl alcohol, t-octanol or .alpha.-terpineol) or an alkene. Preferably, the substrate is an alkene, more preferably, an alkene according to the structural formula (1):

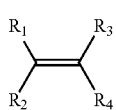
(1)

wherein:
R$_1$ and R$_2$ are each independently (C$_1$-C$_{10}$)alkyl, substituted (C$_1$-C$_{10}$)alkyl, (C$_1$-C$_{10}$) alkenyl or substituted (C$_1$-C$_{10}$)alkenyl; and R$_3$ and R$_4$ are each independently hydrogen or (C$_1$-C$_{10}$)alkyl, substituted (C$_1$-C$_{10}$)alkyl, (C$_1$-C$_{10}$)alkenyl or substituted (C$_1$-C$_{10}$)alkenyl;
or R$_1$ and R$_3$ are joined to form, together with the alkenyl carbons to which they are attached, a (C$_4$-C$_{10}$) cycloalkenyl ring or a substituted (C$_4$-C$_{10}$)cycloalkenyl ring; and
R$_2$ and R$_4$ are each independently hydrogen, (C$_1$-C$_{10}$) alkyl or substituted (C$_1$-C$_{10}$)alkyl.

Preferred alkenes according to structural formula (1) include, for example, isobutene, 2,3-dimethyl-2-butene, 2,3-dimethyl-1-pentene, 2,3-diethyl-1-hexene, 2-methyl-3-ethyl-1-pentene, 2,3,3-trimethyl-1-heptene, 2,3,3,4-tetramethyl-1-hexene, 2,3-dimethyl-1,3-butadiene, 2,5-dimethyl-1,5-hexadiene, 1,3,9-trimethyl cyclododeca-1,3,9-triene, myrcene, cyclohexene, cycloheptene, cyclooctene, terpenes, such as, for example, limonene, alpha-terpineol and delta-carene, alkene oligomers and mixtures thereof. As used herein, the terminology "alkene oligomer" means a compound consisting of a linear, branched or cyclic chain of front 2 to about 20 repeating units derived by polymerizing alkene monomers. Preferably, the alkene is an alkene oligomer, including, for example, dimers; trimers, tetramers and pentamers of propylene, butylene, isobutylene and isoprene. Especially preferred alkenes are butylene dimer, isobutylene dimer, propylene trimer, propylene tetramer, butylene tetramer, isobutylene tetramer, propylene hexamer and mixtures thereof; preferably propylene tetramer, propylene hexamer or isobutylene dimer.

In a preferred embodiment, the substrate compound has more than one reactive site per molecule capable of generating a carbonium ion, including, for example, .alpha.-terpineol, limonene and dimethyl-1,3-butadiene.

Preferably, the strong acid HA is a compound that has a pKa less than about 5, more preferably less than about 2. Suitable strong acids include inorganic acids such as, for example, hydrochloric acid, phosphoric acid, sulfuric acid, organic acids such as, for example, formic acid, methane sulfonic acid, p-toluene sulfonic acid and strongly acidic ion exchange resins such as, for example, AMBERLYST 15 resin (Rohm and Haas Company, Philadelphia, Pa.). Preferably, the strong acid HA is a concentrated aqueous solution of sulfuric acid that includes from about 60 wt % to about 100 wt % sulfuric acid. The reaction mixture includes from about 0.2 moles to about 4 moles, more preferably from about 1 mole to about 2 moles, of the strong acid HA per mole of reactive sites of the substrate compound, wherein the number of moles of reactive sites of the substrate compound equals the product of the number of moles of substrate compound multiplied by the number of reactive sites per molecule of the substrate compound.

Hydrogen cyanide or a salt thereof (collectively "cyanide") is used in the present method. Preferably, hydrogen cyanide is added directly to the reaction mixture. In a preferred embodiment, a salt of hydrogen cyanide under the reaction conditions is added to the reaction mixture and hydrogen cyanide is generated in situ. Preferred salts of hydrogen cyanide include, for example, alkali metal and alkaline earth metal cyanide salts; preferably sodium cyanide or potassium cyanide.

Preferably, the reaction mixture includes from about 1 mole to about 10 moles; preferably from about 1 mole to about 1.5 moles; hydrogen cyanide or an equivalent amount of a cyanide salt per mole of reactive sites of the substrate. Preferably, the reaction mixture of the first step of the process includes from about 0.8 mole to about 10 moles; preferably from about 1 mole to about 3 moles, water per mole of reactive sites of the substrate.

Preferably, the reaction mixture is maintained at a temperature from about 20° C. to about 120° C., more preferably, from about 30° C. to about 60° C., during the first process step. Preferably, the substrate compound is charged to the reaction vessel and the acid and cyanide are fed into the reaction vessel according to feed rate profiles that allow heating of the reaction mixture by reaction exotherm to a selected temperature. Preferably, the reaction mixture is maintained at a pressure from about 1 atmosphere (101 kPa) to about 10 atmospheres (1.01 MPa), preferably about 1 atmosphere (101 kPa), during the first process step. Preferably, the first reaction intermediate is not isolated from the reaction mixture.

In a second step of the method of this invention, the first reaction intermediate is contacted with water to hydrolyze it to the second reaction intermediate. The reaction mixture of the second step of the process includes from about 0.5 mole to about 20 moles, more preferably from about 1 mole to about 10 moles, water per mole of reactive sites of the substrate compound. The reaction mixture is gradually heated to a temperature of from about 50° C. to about 130° C., preferably about 60° C. to about 110° C., during the second process step. The reaction mixture is maintained at a pressure from about 0.1 to about 2 atmospheres (10 kPa to 202 kPa), preferably about 1 atmosphere (101 kPa), during the second process step.

In a third step of the method of this invention, the level of cyanide (preferably hydrogen cyanide) is reduced. The percent reduction is based on the cyanide content of the second reaction intermediate mixture, i.e., the entire product of the second step (hydrolysis), with 100% removal producing a mixture having no cyanide. A hydrogen cyanide stripper may be used for this purpose. Preferably, the hydrogen cyanide stripper is countercurrent contacting device with a top (or near to top) fed feed and a vapor rising from the bottom, either as an inert stripping gas or as a vapor provided by a heat source (reboiler) tower, preferably one having a low process liquid hold-up capacity in order to minimize safety concerns, and a minimum amount of liquid retention in the event of shutdown. A tower provided with either random or structured packing would meet these process needs, as would a tower fitted with a device such as dual-flow trays. Other preferred hydrogen cyanide strippers include a cascade of educators or similar devices arranged in a suitable countercurrent form. In a preferred embodiment of the invention, the hydrogen cyanide level may also be reduced by passing an inert gas, preferably a flammable one, through the reaction mixture containing the second reaction intermediate. The gas containing cyanide vapor may be burned or recycled to a process which consumes cyanide, including the first step of the present method. Preferably, the cyanide present in the second reaction intermediate is reduced to less than 7 ppm cyanide, preferably less than 5 ppm, preferably less than 3 ppm, preferably less than 2 ppm.

In a fourth step of the method of this invention, the second reaction intermediate is neutralized with an alkali metal hydroxide to form the amine. Preferably, the alkali metal is lithium, sodium or potassium; preferably sodium or potassium; preferably sodium. Mixtures of alkali metal hydroxides may be used. Preferably, the molar amount of alkali metal hydroxide is at least equal to the molar amount of acids in the reaction mixture; preferably the molar % excess of alkali metal hydroxide is no greater than 20%, preferably no greater than 15%, preferably no greater than 10%, preferably no greater than 5%. The amount of acid in the reaction mixture is calculated from the acid added in the first step, from both the acid and the hydrogen cyanide, if cyanide is added in the form of hydrogen cyanide.

In the preferred embodiment wherein the substrate is an alkene according to the structural formula (1), the amine is a compound according of the structural formula (2):

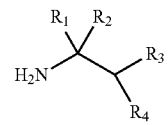

wherein $R_1$, $R_2$, $R_3$, and $R_4$ are each defined as above.

Preferably, the amine is one of the PRIMENE™ amines. The PRIMENE amines are available from Rohm and Haas Company; Philadelphia, Pa. For example, an isomeric mixture of $C_{16}$ to $C_{22}$ tertiary alkyl primary amines (PRIMENE JM-T amine); an isomeric mixture of $C_8$ to $C_{10}$ tertiary alkyl primary amines (PRIMENE BC-9 amine); an isomeric mixture of $C_{10}$ to $C_{15}$ tertiary alkyl primary amines (PRIMENE 81-R amine); or mixtures thereof; tert-octyl amine (PRIMENE TOA amine). In some PRIMENE amines, the amine is a diamine in which each amino group is attached to a tertiary alkyl group. An example of such an amine is PRIMENE MD amine, available from Rohm and Haas Company; Philadelphia, Pa.

EXAMPLES

Modeling of distillation column for stripping HCN from a simulated system comprising tert-butyl formamide and n-octane.

Exploratory simulations of the atmospheric pressure HCN stripper showed the HCN specification to be met using a fairly small diameter column with low energy requirements. Given the small column dimensions, low energy consumption, and small amount of HCN removal required, a simulation was completed with a reflux ratio of 100 to try and minimize the amount of overhead stream. Table 1 shows the feed, overhead, and bottoms compositions and temperatures.

TABLE 1

HCN Stripper Stream Compositions and Temperatures from ASPEN Plus Simulations

| | FEED | OVHDS | BTTMS |
|---|---|---|---|
| Temperature, C. | 100 | 58.7 | 115.8 |
| Pressure, $N/m^2$ | 101325 | 101325 | 101325 |
| Vapor Fraction | 0 | 0 | 0 |
| Mole Flow, kmol/hr | 54.87 | 0.28 | 54.59 |
| Mass Flow, kg/hr | 2764.5 | 9.1 | 2755.4 |
| Volume Flow, $m^3$/hr | 2.86 | 0.01 | 2.90 |
| Enthalpy, MMBtu/hr | −20.1 | −0.038 | −19.9 |
| Mass Flow kg/hr | | | |
| WATER | 528.0 | 2.4 | 525.5 |
| HCN | 2.8 | 2.8 | trace |
| Formic Acid | 263.1 | 0.4 | 262.6 |
| t-butyl formamide | 1082.6 | 0.1 | 1082.7 |
| $H_2SO_4$ | 878.6 | trace | 878.6 |
| N-OCTANE | 9.3 | 3.4 | 5.9 |

Under the high-reflux conditions, the simulation results indicate that the overhead stream is only 0.3% of the feed stream and removes almost 99.9% of the HCN. Only ~2.8 kg/hr of HCN is removed overhead out of a column feed rate of ~2765 kg/hr. The feed was introduced to the column at the $2^{nd}$ stage (near the top) of a 14 theoretical stage still. Column diameter ranged from 1.2 to 1.6 ft (0.36 to 0.48 m) depending on whether trays or packing was selected. Table 2 shows the concentrations of the components at each theoretical stage.

TABLE 2

Mass Fraction Component Concentrations in the Still

| Stage | WATER | hydrogen cyanide | formic acid | t-butyl formamide | sulfuric acid | n-octane |
|---|---|---|---|---|---|---|
| 1 | 0.067664 | 0.811602 | 0.004421 | 3.15E−05 | 4.81E−11 | 0.116282 |
| 2 | 0.277037 | 0.304848 | 0.048495 | 0.0085838 | 1.75E−05 | 0.361018 |
| 3 | 0.307929 | 0.143593 | 0.054365 | 0.00890478 | 2.08E−05 | 0.485188 |
| 4 | 0.318591 | 0.068843 | 0.056564 | 0.00883631 | 2.20E−05 | 0.547143 |
| 5 | 0.322866 | 0.033965 | 0.057486 | 0.00875134 | 2.24E−05 | 0.576909 |
| 6 | 0.3251 | 0.017079 | 0.057898 | 0.00870988 | 2.25E−05 | 0.59119 |
| 7 | 0.327034 | 0.008683 | 0.058058 | 0.00872794 | 2.28E−05 | 0.597474 |
| 8 | 0.330631 | 0.004442 | 0.058169 | 0.00886034 | 2.32E−05 | 0.597874 |
| 9 | 0.339859 | 0.002284 | 0.058628 | 0.00926975 | 2.45E−05 | 0.589934 |
| 10 | 0.36375 | 0.001179 | 0.060585 | 0.01037216 | 2.80E−05 | 0.564086 |
| 11 | 0.420735 | 0.000607 | 0.066985 | 0.01300314 | 3.66E−05 | 0.498633 |
| 12 | 0.528861 | 0.0003 | 0.08145 | 0.01792189 | 5.34E−05 | 0.371414 |
| 13 | 0.663186 | 0.00013 | 0.10265 | 0.02401493 | 7.52E−05 | 0.209944 |
| 14 | 0.756781 | 4.66E−05 | 0.127956 | 0.02912022 | 9.29E−05 | 0.086003 |
| 15 | 0.751265 | 1.27E−05 | 0.16916 | 0.05647482 | 0.000224 | 0.022863 |

Note, the HCN concentration in the stripper bottoms is at the design specification of the column, 1 ppm, rendering concern about polymerization moot. Concern about HCN polymerization in the HCN stripper overheads is also minimal since the temperature in the stripper overheads is only about 140° F. (60.5° C.), significantly lower than the existing Hydrolysis overheads of 220 to 230° F. (104 to 110° C.). Recycling the condensed overheads back to the first Generation reactor was evaluated. Table 3 shows a comparison between the normal feed rate to the first Generation Reactor and the flow rate from the proposed HCN overhead stripper stream.

TABLE 3

Comparison Between the Flow Rate to the First Generation Reactor and HCN Stripper Overhead Stream

| Components | Generation Feed, kg/hr | HCN Stripper Overhead, kg/hr | Overhead/ Generation Fraction |
|---|---|---|---|
| water | 127.3 | 2.7 | 0.021 |
| HCN | 185.0 | 2.3 | 0.012 |
| Formic Acid | 0 | 0.5 | 0 |
| t-butyl formamide | 0 | 0.1 | 0 |
| H$_2$SO$_4$ | 852.3 | 0 | 0 |
| N-octane (Protet) | 1000 | 3.6 | 0.004 |
| Total flow rate | 2037.3 | 9.1 | 0.004 |

Flow rate of the overhead stream is ~0.4% of the total feed to the first Generation reactor.

Neutralization of PRIMENE Amine Process Streams with NaOH

The process stream(s) collected from the amine production unit were charged in a two neck round bottom flask. The flask was equipped with a packed column, a distillate head (Ace Glass catalog #6613-12, distilling head, vacuum type), with a finger type condenser and 0-3 mm PTFE stopcock for reflux control. Glass stop cocks on the manifold and reflux arms were used to isolate the head from the receiver so that the receiver's contents could be removed without disturbing the vacuum in the system. The distilling head had a condenser on the takeoff arm and a 10/30 thermometer joint with a 76 mm immersion thermometer. Both column joint and receiver joint were 24/40. The finger condenser was approx. 20.3 cm long with a 24/40 joint and was attached at the top of the column having chilled water circulation at 6° C. temperature. A jacketed receiving funnel was attached at the end of the distillate head to receive the overhead. The receiving jacked was kept cold via cold water circulation to prevent the evaporation of the volatile overhead. The vacuum line was connected to a standard dry-ice trap system. The vacuum pump was started and the bleed valve adjusted such that the vacuum gauge showed 60 mm Hg. The system was under vacuum during the distillation. The mixture in the flask was mixed using a magnetic stirrer and the flask was heated in an oil bath to 110° C. to 125° C. to remove the volatiles. The heating bath was placed on a magnetic stir plate. The oil bath was stirred with a magnetic stir bar. At the end of the experiment, the overhead was transferred into a special glass bottle and the bottle was either stored in a freezer, or neutralized with caustic (aq. NaOH) and discarded. The glass bottle was rated for pressure, 200 psi. The stripped hydrolysis stream was neutralized with caustic to obtain the crude amine and aqua salt stream. The starting hydrolysis stream, the stripped hydrolysis stream, and aqua salt stream from caustic neutralization were analyzed for cyanide content.

Neutralization of the stripped hydrolysis stream was carried out using 25% caustic. The stream was transferred into a round bottom flask with a bottom stopcock. The flask was equipped with a heating jacket, a mechanical stirrer with an adjustable speed, a condenser, a temperature thermocouple, and a feed funnel. A calculated amount of 25% caustic was transferred to the feed funnel. The caustic was added into the flask while stirring and maintaining the temperature at 90° C. Heat was applied via a heating jacket at the end of the neutralization if the temperature was lower than 90° C. The mixture was stirred for 15 minutes after all the caustic was added. At the end of stirring period, the mechanical stirrer was stopped to allow the mixture to separate into two layers for 15 minutes. The layers were carefully separated and their weights recorded.

Benefit of Using NaOH Over Ammonia (pH of Aqueous Layer >9.5); Concentration of Amine in Aqueous Waste Stream from Neutralization

| PRIMENE amine | $NH_3$ Neutralization | NaOH |
|---|---|---|
| 81R | 500 to 1000 ppm (0.4%) | Non-detectable (none) |
| TOA | 2 wt. % (3.0%) | 0.25 wt. % (1.9%) |

Note:
first number is amine concentration, number in parentheses is the wt % of amine lost in the waste stream, based on the entire theoretical amount of amine Treatment of Aqueous Waste Stream from Neutralization PRIMENE 81R Amine Aqueous Waste Biotreatability GC/MS analysis of the HCN stripped/NaOH neutralized indicated the waste stream samples contained non-detectable amounts of amine. Respirometry tests were completed on this material to determine if any of the other possible components were biodegradable. Results indicated that the materials were biodegradeable.

The COD of the wastewater was biodegradable.

Oxygen uptake values of 81 to 89% of the applied tCOD were observed for the 50%, 100% and 200% conditions (% of normal flow).

Soluble COD measurements taken at the end of these tests showed COD removals increasing from 30% for the 50% waste water dose to 56% for the 100% condition to 70% for the 200% condition. It is likely that this trend was caused by the high residual sCOD, some of which appears to have come from a source other than the waste water. Because the percent removal was calculated using the tCOD added with the waste water and did not include any other contributions the high residual would have a greater effect of reducing observed % COD removal for the low dose tests then the high dose tests. Additional testing would be required to identify the cause of the high residual sCOD.

|  | units | 50% | 100%* | 200% |
|---|---|---|---|---|
| tCOD added (waste water) | mg/L | 222 | 444 | 887 |
| sCOD added (waste water) | mg/L | 221 | 442 | 884 |
| final sCOD |  | 146 | 193 | 307 |
| % removal for COD** |  | 30% | 56% | 70% |
| Final seed corrected OU | mg/L | 196 | 360 | 786 |
| OU as % of tCOD added*** |  | 89% | 81% | 89% |

*100% load is for PRIMENE 81R amine aqueous waste being 1.9% of total wastewater flow.
**% removal for COD = (initial tCOD − final sCOD)/initial tCOD
***OU as % of tCOD added = Final seed corrected OU/tCOD added
OU = Oxygen uptake;
tCOD = total Chemical Oxygen Demand;
sCOD = soluble Chemical Oxygen Demand

The invention claimed is:

1. A method for producing an amine; said method comprising steps of: (a) contacting hydrogen cyanide or a salt thereof, an acid, water and a substrate compound capable of generating a carbonium ion by reaction with the acid to generate a first reaction intermediate; (b) contacting the first reaction intermediate with water to form a second reaction intermediate; (c) removing hydrogen cyanide present in the second reaction intermediate to a concentration less than 10 ppm; and (d) contacting the second reaction intermediate with an alkali metal hydroxide to form the amine; wherein hydrogen cyanide is removed from the second reaction intermediate by a stripper column and hydrogen cyanide removed from the second reaction intermediate is recycled to step (a).

2. The method of claim 1 in which the substrate compound is an alkene oligomer.

3. The method of claim 2 in which the acid is an inorganic acid.

4. The method of claim 3 in which the alkali metal hydroxide is sodium hydroxide or potassium hydroxide.

5. The method of claim 4 in which the alkene oligomer is propylene tetramer, propylene hexamer or isobutylene dimer.

6. The method of claim 5 in which the inorganic acid is a concentrated aqueous solution of sulfuric acid that includes from about 60 wt % to about 100 wt % sulfuric acid.

7. A method for producing an amine; said method comprising steps of: (a) contacting: (i) hydrogen cyanide or a salt thereof, (ii) a concentrated aqueous solution of sulfuric acid that includes from about 60 wt % to about 100 wt % sulfuric acid, (iii) water and (iv) propylene tetramer, propylene hexamer or isobutylene dimer to generate a first reaction intermediate; (b) contacting the first reaction intermediate with water to form a second reaction intermediate; (c) removing cyanide present in the second reaction intermediate to a concentration less than 10 ppm; and (d) contacting the second reaction intermediate with sodium hydroxide or potassium hydroxide to form the amine; wherein hydrogen cyanide is removed from the second reaction intermediate by a stripper column and hydrogen cyanide removed from the second reaction intermediate is recycled to step (a).

* * * * *